(12) United States Patent
Riley

(10) Patent No.: US 7,308,985 B2
(45) Date of Patent: Dec. 18, 2007

(54) PACKAGING FOR A KIT, AND RELATED METHODS OF USE

(75) Inventor: Kimberly Riley, Boylston, MA (US)

(73) Assignee: Scimed Life Systems, Inc., Maple Grove, MN (US)

( * ) Notice: Subject to any disclaimer, the term of this patent is extended or adjusted under 35 U.S.C. 154(b) by 531 days.

(21) Appl. No.: 10/890,135

(22) Filed: Jul. 14, 2004

(65) Prior Publication Data
US 2006/0011506 A1  Jan. 19, 2006

(51) Int. Cl.
*B65D 69/00* (2006.01)
(52) U.S. Cl. .................. 206/570; 206/438; 206/363
(58) Field of Classification Search ............ 206/363, 206/365, 366, 369, 370, 438, 570, 571, 572, 206/477; 53/443
See application file for complete search history.

(56) References Cited

U.S. PATENT DOCUMENTS

| | | | | |
|---|---|---|---|---|
| 4,135,868 A | * | 1/1979 | Schainholz | 422/310 |
| 4,573,569 A | * | 3/1986 | Parker | 206/1.7 |
| 5,681,539 A | * | 10/1997 | Riley | 422/300 |
| 5,971,152 A | * | 10/1999 | Bowsman | 206/438 |
| 6,588,587 B2 | * | 7/2003 | Johnson et al. | 206/363 |
| 2002/0185406 A1 | * | 12/2002 | Massengale et al. | 206/571 |
| 2004/0195131 A1 | * | 10/2004 | Spolidoro | 206/438 |
| 2004/0238391 A1 | * | 12/2004 | Pond | 206/369 |

* cited by examiner

*Primary Examiner*—David T. Fidei
(74) *Attorney, Agent, or Firm*—Finnegan, Henderson, Farabow, Garrett, & Dunner, L.L.P.

(57) ABSTRACT

Embodiments of the invention include a packaging for a medical kit. The packaging includes a bottom configured to receive a plurality of medical products and a top having at least one protrusion extending therefrom. The bottom and the top are shaped so that the bottom receives the top with the at least one protrusion extending towards the bottom. The at least one protrusion is configured to deform about the plurality of medical products to restrict movement of the plurality of medical products.

37 Claims, 3 Drawing Sheets

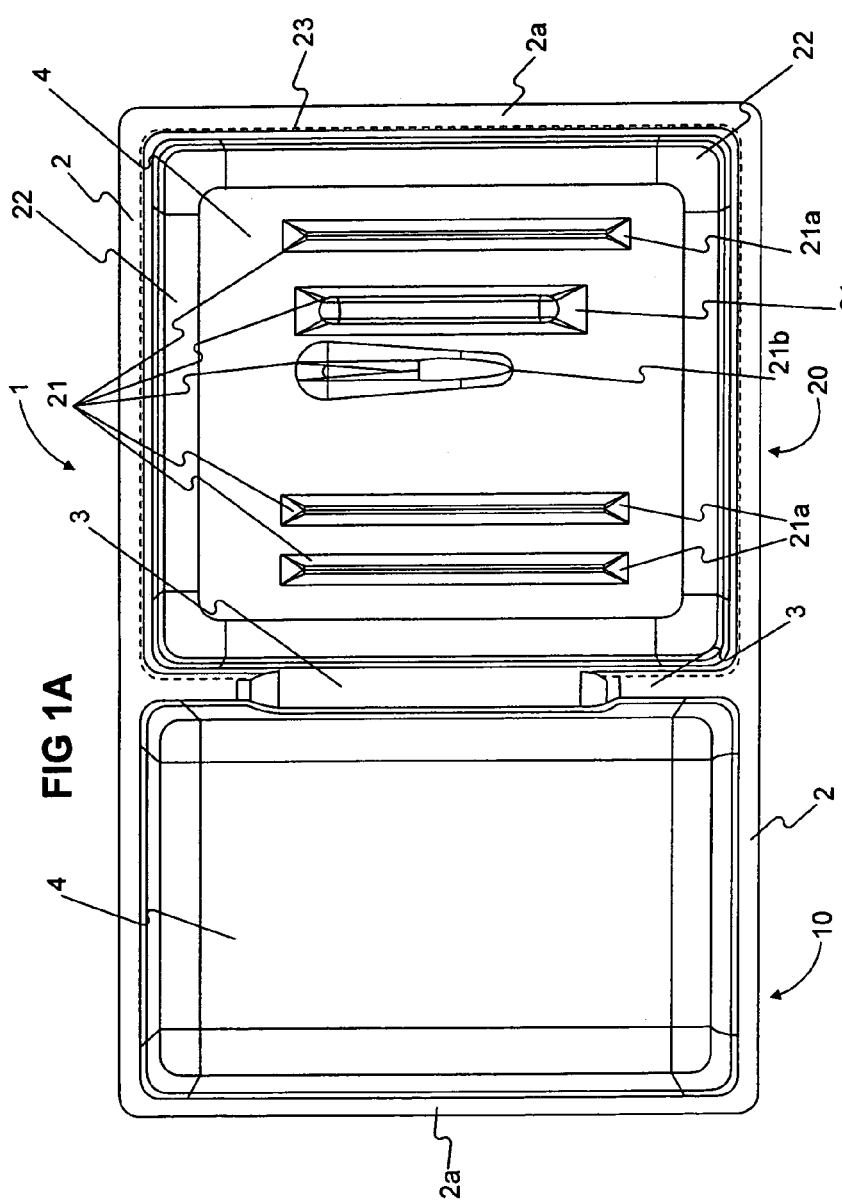
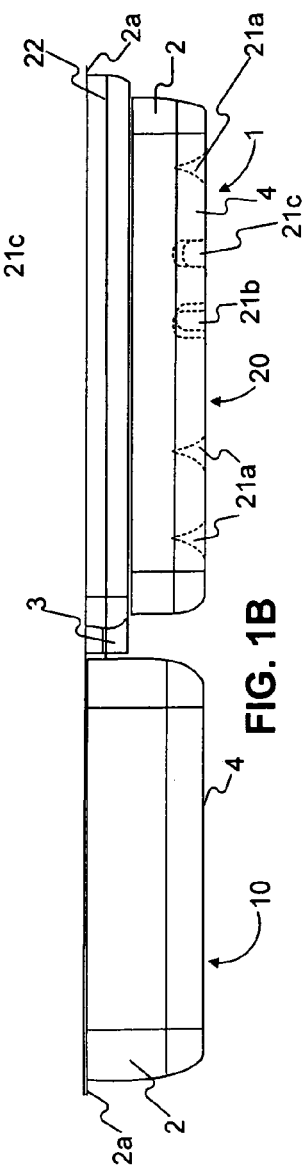
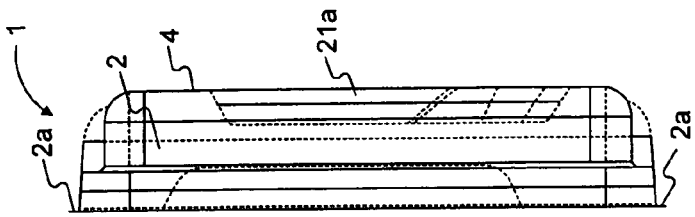
FIG. 1A
FIG. 1B
FIG. 1C

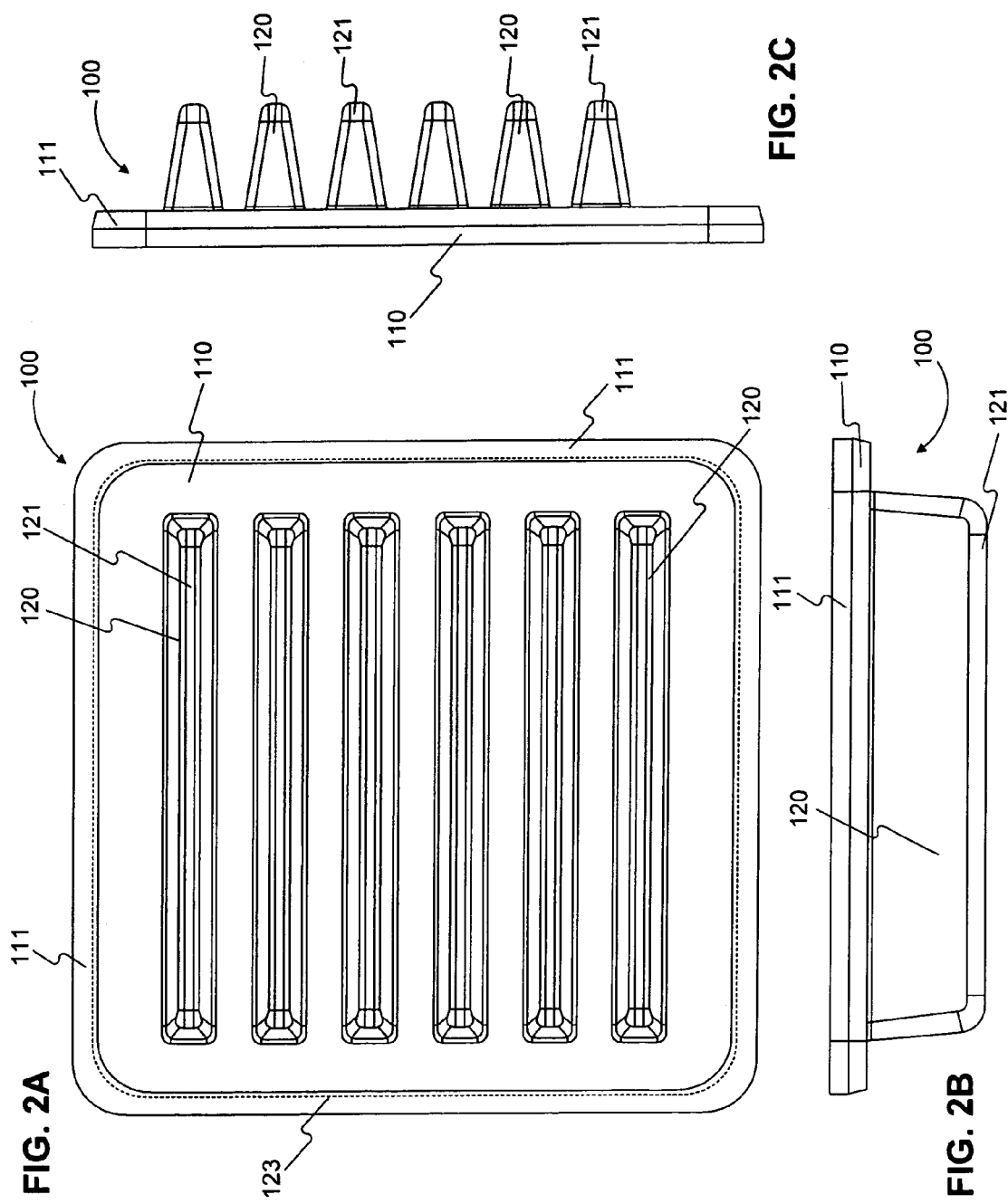

PACKAGING FOR A KIT, AND RELATED METHODS OF USE

DESCRIPTION OF THE INVENTION

1. Field of the Invention

Embodiments of the invention include a packaging for securing kit contents, and methods of use thereof. In particular, embodiments of the invention include a packaging for medical components, the packaging being configured to secure one of a variety of medical kits having differing components.

2. Background of the Invention

Various medical procedures need several medical devices and/or components to perform the procedure. Some of the medical devices or components may be specifically adapted for a particular medical procedure, while other medical devices or components may be used in several different medical procedures.

To facilitate the performance of a particular medical procedure, the particular medical kit contents (e.g., devices, components, accessories, compounds, chemicals, drugs) necessary for the procedure may be provided together in the form of a kit. In this way, the medical practitioner performing the procedure does not need to independently obtain each medical kit content necessary for the procedure, saving time and also reducing the likelihood that the medical practitioner will realize during the procedure that a desired medical kit content was not provided.

One medical procedure where a kit may be provided and used is an enteral or intestinal feeding procedure. Enteral feeding is generally considered for patients with swallowing disorders that are so severe, they are unable to take adequate nutrition safely by mouth. Examples of such swallowing disorders include neurogenic or postoperative dysphagia. Enteral feeding, most often provided by an endoscopically placed gastrostomy tube, provides a means of assuring adequate nutrition and decreasing the severity of aspiration. While the patient is being enterally fed, measures are often taken to correct the swallowing problem.

An enteral feeding procedure may require the use of one or more of the following medical kit contents: syringe(s), sponge(s), oral care kit(s), tape(s), wipe(s), catheter(s), catheter plug(s), cream(s), periwash(es), feeding bag(s), Q-tip (s), container(s) (for example, containing formula(s) to be enterally fed to the patient), tube(s), trachea tube holder(s), clamp(s), roller clamp(s), hanging ring(s), pump(s), ice pouch(es), port(s), balloon(s), safety needle(s), prefilled syringe(s), connector(s), cap(s), or other known medical kit contents used in enteral feeding procedures.

One or more of the aforementioned medical kit contents may be provided in a prepackaged kit, for example, by providing them in a single container. The container may include a thermoformed packaging that is adapted to accommodate a specific combination of the aforementioned medical kit contents in specific orientations. The thermoformed packaging may be configured to accommodate the medical kit contents of the enteral feeding kit such that it protects the medical kit contents during handling and transportation prior to use.

Because the thermoformed packaging is specifically configured to accommodate the specific combination of the aforementioned medical kit contents in specific orientations, however, the thermoformed packaging sometimes forms a tight snap-fit and/or press-fit with a particular medical kit content that makes it difficult to remove the medical kit content from the thermoformed packaging.

Moreover, each time a new combination of medical kit contents for an enteral feeding kit is provided or a particular medical kit content is redesigned, a new thermoformed packaging needs to be designed and manufactured so as to accommodate the new combination or newly designed medical kit content. Such redesigning of the thermoformed packaging can be lengthy, require the expenditure of resources, and potentially delay commercial launch of the new enteral feeding kit

SUMMARY OF THE INVENTION

In accordance with the invention, an embodiment of the invention includes a packaging for a medical kit. The packaging includes a bottom configured to receive a plurality of medical products and a top having at least one protrusion extending therefrom. The bottom and the top are shaped so that the bottom receives the top with the at least one protrusion extending towards the bottom. The at least one protrusion is configured to deform about the plurality of medical products to restrict movement of the plurality of medical products.

Another embodiment of the invention includes a packaging for a set of medical products. The packaging includes a housing portion configured to loosely receive the set of medical products and a retaining portion configured to be secured to the housing portion with the set of medical products between the retaining portion and the housing portion. The retaining portion has an initial configuration not corresponding to a configuration of the set of medical products. The initial configuration of the retaining portion is capable of changing as the retaining portion is secured to the housing portion to restrict movement of the set of medical products.

A further embodiment of the invention includes a packaged medical kit. The packaged medical kit includes a plurality of medical products, a bottom containing the plurality of medical products, and a top received by the bottom and having at least one protrusion extending substantially toward the bottom. The bottom is configured to loosely receive the plurality of medical products when the bottom has not received the top. The at least one protrusion is deformed about the plurality of medical products to restrict movement of the plurality of medical products.

Still another embodiment of the invention includes a packaged medical kit. The packaged medical kit includes a set of medical products, a housing portion containing the set of medical products, and a retaining portion secured to the housing portion with the set of medical products between the retaining portion and the housing portion. The retaining portion has an initial configuration not corresponding to a configuration of the set of medical products prior to the retaining portion being secured to the housing portion. The initial configuration of the retaining portion changes to correspond to the configuration of the set of medical products as the retaining portion is secured to the housing portion to restrict movement of the set of medical products.

Various embodiments of the invention may have any or all of the following features: the bottom may be configured to loosely receive the plurality of medical products; the bottom may include at least one protrusion extending towards the top, the at least one protrusion of the bottom configured to loosely separate the plurality of medical products; the bottom and the top may be configured such that when the bottom receives the top, the at least one protrusion of the bottom is substantially transverse to the at least one protrusion of the top; the at least one protrusion may include at least two protrusions having different shapes; the at least one protrusion may include at least two protrusions having different shapes; the at least one protrusion may be comprised of PETG; at least a portion of the top may configured to form a snap-fit with at least a portion of the bottom; the initial configuration of the retaining portion may be capable of changing as the retaining portion is secured to the housing portion to restrict movement of another set of medical products having a different configuration from the set of medical products; the retaining portion may include at least one protrusion configured to deform as the retaining portion is secured to the housing portion to restrict movement of the set of medical products; the at least one protrusion may include at least two protrusions having different shapes; the housing portion may include at least one protrusion configured to loosely receive the set of medical products; the at least one protrusion may include at least two protrusions having different shapes; the housing portion may include at least one protrusion configured to loosely receive the set of medical products; the housing portion and the retaining portion may be configured such that when the housing portion receives the retaining portion, the at least one protrusion of the housing portion is substantially transverse to the at least one protrusion of the retaining portion; the at least one protrusion may be comprised of PETG; at least a portion of the housing portion may be configured to form a snap-fit with at least a portion of the retaining portion.

A still further embodiment includes a method of packaging a medical kit. The method includes providing a packaging for a medical kit. The packaging includes a bottom configured to receive a plurality of medical products and a top having at least one protrusion extending therefrom. The method also includes arranging the plurality of medical products in the bottom and securing the top to the bottom such that the at least one protrusion extends toward the bottom and deforms about the plurality of medical products to restrict movement of the plurality of medical products.

Yet another embodiment includes a method of packaging a set of medical products. The method includes providing a packaging for the set of medical products. The packaging includes a housing portion configured to loosely receive the set of medical products and a retaining portion configured to be secured to the housing portion with the set of medical products between the retaining portion and the housing portion, the retaining portion having an initial configuration not corresponding to a configuration of the set of medical products. The method also includes providing the set of medical products, arranging the set of medical products in the housing portion, and securing the retaining portion to the housing portion such that the initial configuration of the retaining portion changes to correspond to the configuration of the set of medical products as the retaining portion is secured to the housing portion to restrict movement of the set of medical products.

Various embodiments of the invention may have any or all of the following features: securing the top to the bottom may include applying pressure to at least one of the top and the bottom; securing the top to the bottom may include forming a snap-fit between the top and the bottom; arranging may include loosely arranging the plurality of medical products in the bottom; the bottom may include at least one protrusion extending towards the top, the at least one protrusion of the bottom configured to loosely separate the plurality of medical products; the bottom and the top may be configured such that when the bottom receives the top, the at least one protrusion of the bottom is substantially transverse to the at least one protrusion of the top; securing the retaining portion to the housing portion may include applying pressure to at least one of the retaining portion and the housing portion; securing the retaining portion to the housing portion may include forming a snap-fit between the retaining portion and the housing portion; securing the retaining portion to the housing portion may include deforming at least one protrusion on the retaining portion around the set of medical products; arranging may include loosely arranging the plurality of medical products in the housing portion; the housing portion may include at least one protrusion extending towards the top, the at least one protrusion of the housing portion configured to loosely separate the plurality of medical products; the housing portion and the retaining portion may be configured such that when the housing portion receives the retaining portion, the at least one protrusion of the housing portion is substantially transverse to the at least one protrusion of the retaining portion.

Additional objects and advantages of the invention will be set forth in part in the description which follows, and in part will be obvious from the description, or may be learned by practice of the invention. The objects and advantages of the invention will be realized and attained by means of the elements and combinations particularly pointed out in the appended claims.

The foregoing general description and the following detailed description are exemplary and explanatory only and are not restrictive of the invention, as claimed.

BRIEF DESCRIPTION OF THE DRAWINGS

The accompanying drawings, which are incorporated in and constitute a part of this specification, illustrate embodiments of the invention and together with the description, serve to explain the principles of the invention.

FIGS. 1A-1C are various schematic views of a kit tray, according to an embodiment of the invention.

FIGS. 2A-2C are various schematic views of a kit retainer for use with the kit tray of FIGS. 1A-1C, according to an embodiment of the invention.

DESCRIPTION OF THE EMBODIMENTS

Figure 3:
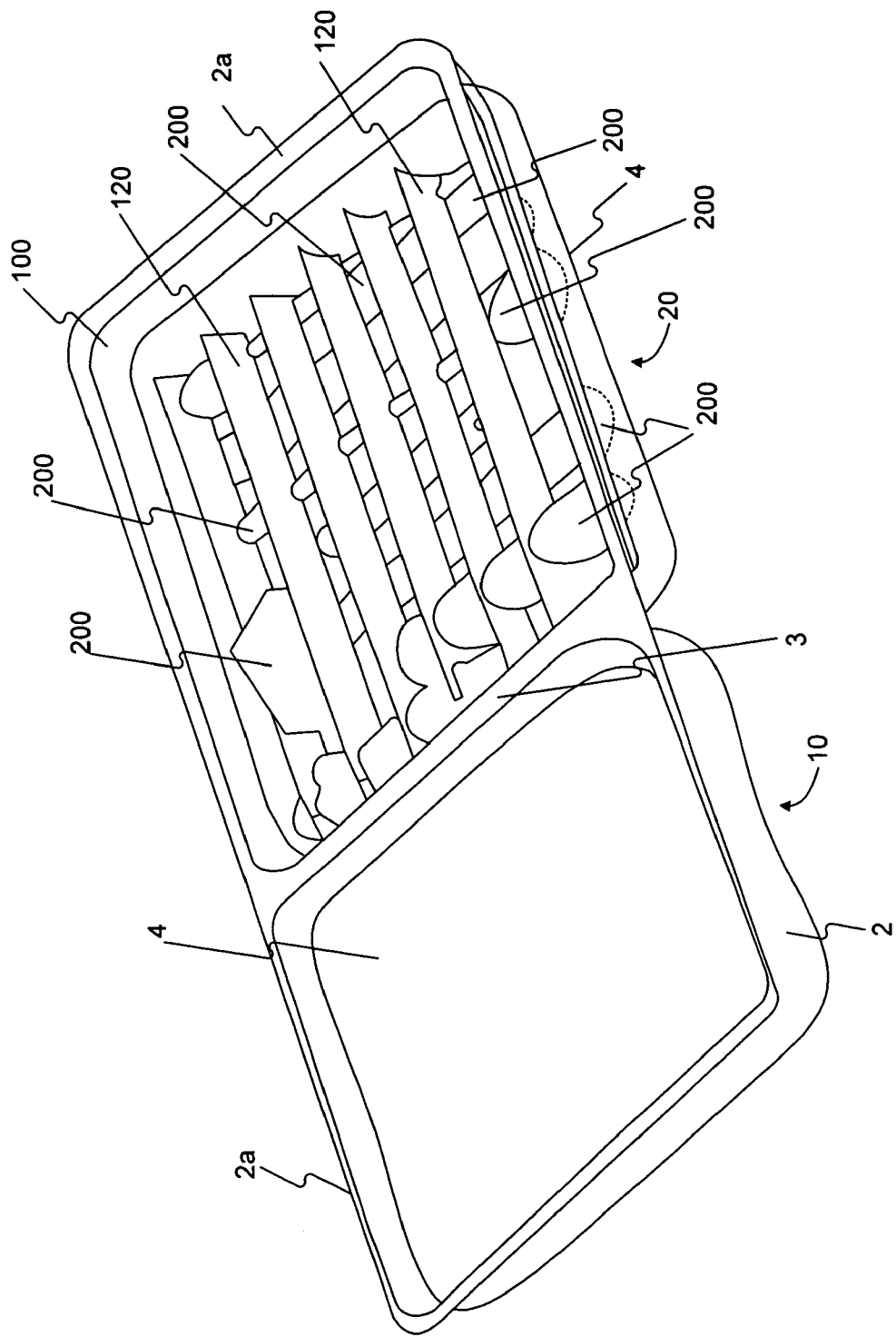
FIG. 3 is a perspective view of the kit tray of FIGS. 1A-1C secured to the kit retainer of FIGS. 2A-2C with kit contents secured in between, according to an embodiment of the invention.

Reference will now be made in detail to the present exemplary embodiments of the invention illustrated in the accompanying drawings. Wherever possible, the same reference numbers will be used throughout the drawings to refer to the same or like parts.

An exemplary embodiment of a kit tray is depicted in FIGS. 1A-1C. The kit tray 1 (or bottom) may include a working portion 10 and a kit content housing portion 20. The working portion 10 and the kit content housing portion 20 may be defined by an outer side wall 2 extending around the working portion 10 and the kit content housing portion 20, an inner wall 3 extending between the working portion 10 and the kit content housing portion 20, and floor portion 4 that defines the bottom of the working portion 10 and the kit content housing portion 20. The outer side wall 2 may extend into and/or be integrally formed with a lip 2a which extends around the kit tray 1. The inner wall 3 may extend between opposite sides of the kit tray 1, for example extending between opposing lips 2a, and may have differing heights along different portions of the inner wall 3 between the opposing sides of the kit tray.

The working portion 10 may be configured to accommodate any material(s) used during any desired procedure. For example, the working portion 10 may be configured to accommodate one or more medical materials being used during an enteral feeding procedure. The working portion 10 may be generally configured as a cavity and/or a bowl, for example, to hold fluids, waste, or medical devices or components and/or impede materials placed in the working portion 10 from falling out of the working portion 10. The material working portion 10 may have any suitable length, width, height, depth, shape, and/or geometric configuration.

The kit content housing portion 20 may be configured to accommodate any kit content(s) used during any desired procedure. The kit content housing portion 20 may also be configured to store and/or house the kit content(s), for example, during storage and/or transportation. The kit content housing portion 20 may be generally configured as a cavity and/or a bowl, for example, to impede kit contents placed in the kit content housing portion 20 from falling out of the housing portion 20. Kit content housing portion 20 may have any suitable length, width, height, depth, shape, and/or geometric configuration.

The kit content housing portion 20 may also have one or more protrusions 21 configured to accommodate, store, and/or house various kit contents. For example, the one or more protrusions 21 may be configured to accommodate, store, and/or house any of the enteral feeding kit contents set forth above. As an example, the two protrusions 21a nearest the working portion 10 may be configured to accommodate, store, and/or house an elongate round object, such as a syringe, between them. FIG. 1A shows five such protrusions 21. Housing portion 20, however, may include more or less protrusions depending, for example, on the number of kit contents. As shown in FIGS. 1A-1C, the protrusions 21a, 21b, 21c may have any desired length, width, height, and/or geometric shape. For example, some of the protrusions 21a may have substantially the same configuration, while other protrusions 21b, 21c may have different configurations. The length, width, height, shape, and/or geometric configuration of the protrusions 21 may be varied, for example, to accommodate any desired object and/or material. The one or more protrusions 21 may be configured to separate kit contents as they are placed in the kit tray 1, to allow the desired object and/or kit content to be wrapped around the one or more protrusions 21, to allow the protrusions 21 to be placed inside the desired object and/or kit content, and/or to form a loose fit with the desired object and/or kit content. The one or more protrusions 21 may generally be in the shape of a shallow rail.

The kit content housing portion 20 may also have an interface portion 22 configured to accommodate, interface with, and/or secure a kit retainer, for example, the kit retainer depicted in FIGS. 2A-2C. The interface portion 22 may be defined by portions of the outer wall 2, inner wall 3, and/or floor 4. The interface portion 22 may also include the perimeter of the kit content housing portion 20. The interface portion 22 may receive the kit retainer shown in FIGS. 2A-2C, and the cooperation between the kit retainer protrusions (to be described), the kit housing portion 20 (such as protrusions 21), and/or the enclosed medical components may provide a secure fit between the retainer and the housing portion 20. Alternatively or additionally, the interface portion 22 may be configured to form a snap-fit and/or press-fit with the kit retainer depicted in FIGS. 2A-2C so as to retain the kit retainer during handling, transportation, and/or jostling. For example, housing portion 20 may include a snap ring 23 extending around a perimeter of housing portion 20. The snap ring 23 may be integrally formed as a part of the interface portion 22, or may be formed separately and then integrated with interface portion 22. The snap ring 23 may be configured to interact with a portion of the kit retainer so as to snap and hold the kit retainer in place relative to the housing portion 20. As another example, at least the interface portion 22 of the kit housing portion 20 may have a cross-sectional area slightly smaller than the kit retainer, may have a geometry conducive to forming a snap-fit and/or press-fit, and/or may have any other snap-fit and/or press-fit accommodating configuration known in the art. The interface portion 22 need not be configured to form a snap-fit and/or press-fit with the kit retainer, as another means may be used to secure the kit retainer to the kit tray. For example, adhesives may be applied to the interface portion and/or kit retainer, the kit tray and kit retainer may be wrapped, the kit tray and kit retainer may be placed in another container, and/or mechanical means (such as clamps or clips) may be used to further secure the kit retainer to the kit tray.

The kit tray may be made out of any suitable material(s) and may be manufactured using any suitable method. Examples of suitable materials include plastic, thermoplastic, rubber, metal, and/or glass. For example, at least a portion of the kit tray may be made of a substantially rigid plastic such as 0.030 CL BAREX, or other materials that may be used as medical device packaging. Examples of suitable methods of manufacture include thermoforming, stamping, press-forming, injection molding, and/or machining. Various portions of the kit tray may be made out of different materials (or mixtures of materials) and/or may be manufactured using different methods. In another example, more than one method may be used to manufacture the kit tray and/or a portion of the kit tray.

An exemplary embodiment of a kit retainer is depicted in FIGS. 2A-2C. The kit retainer 100 (or top or lid) may include a main body portion 110 and one or more protrusions 120. The main body portion 110 may be integrally formed with the one or more protrusions 120 and/or may be configured to accommodate the protrusions 120.

The main body portion 110 may be configured to be placed into a portion of the kit tray 1. For example, an interface portion 111 of the main body portion 110 may be configured to be placed within the interface portion 22 of the kit tray 1. The interface portion 111 may form a snap-fit and/or press-fit with the interface portion 22 of the kit tray 1, for example, so that the kit tray 1 and kit retainer 100 stay together despite jostling during handling and/or transportation. For example, retainer 100 may include a snap ring 123 extending around a perimeter of retainer 100. The snap ring 123 may be integrally formed as a part of the retainer 100, or may be formed separately and then integrated with retainer 100. The snap ring 123 may be configured to interact with a portion of the housing portion 20 (e.g., snap ring 23) so as to snap and hold the kit retainer 100 in place relative to the housing portion 20. For example, the snap rings 23, 123 may use friction to hold and retain the retainer 100 in the housing portion 20. The main body portion 110 may have a substantially flat surface from which the protrusions 120 extend. The main body portion 110, or any portion thereof, may have any suitable length, width, height, depth, shape, and/or geometric configuration, including a configuration that corresponds to that of housing portion 20.

The one or more protrusions 120 may extend from the main body portion 110. The one or more protrusions 120 may be substantially elongate with a round bottom portion 121 as shown in FIGS. 2A-2C, and an open top adjacent the surface of body portion 10. One or more protrusions 120 may have any suitable length, width, height, depth, shape, and/or geometric configuration. The one or more protrusions 120 may also be combined to form any suitable length, width, height, depth, shape, and/or geometric configuration. FIG. 2A shows six such protrusion aligned with one another. Retainer 100, however, may include more or less protrusions.

The protrusions 120 are configured to be deformed, crushed, and/or otherwise altered when pressure is applied to them, for example, against an object and/or kit content. The protrusions 120 may also be configured to substantially return to their original configuration when the pressure is removed, for example, when the retainer 100 is removed from housing portion 20 and its contents. The protrusions 120 may be configured to substantially restrict movement of objects and/or kit contents that are pressed into and/or applying pressure to the protrusions 120. The protrusions 120 may also be configured to protect objects and/or kit contents that are pressed therein and/or that apply pressure thereto, for example, by being formed of a material that is softer than the object and/or kit content. Thus, the protrusions 120 may allow minimal movement of the objects and/or kit contents that are pressed therein and/or apply pressure thereto so as to prevent damage to the objects, for example, when the kit tray 1 and kit retainer 100 containing the objects are jostled during handling and/or transportation.

The protrusions 120 are configured to cooperate with portions of the kit tray 1 and/or medical kit contents contained therein to accommodate, secure, and/or protect the medical kit contents. For example, desired objects and/or kit contents (e.g., one or more of the kit contents used in an enteral feeding procedure) may be accommodated, secured, and or protected by being placed between the floor 4 of the kit tray 1 and the protrusions 120. In such a configuration, the combination of the floor 4 and the deformed protrusions 120 may substantially prevent the movement and/or damage of the desired objects and/or kit contents. As shown in FIG. 3, the protrusions 21 of the kit tray 1 may be oriented transverse to, and substantially perpendicular to, the protrusions 120 of the kit retainer 100. Based on many factors, the protrusions 21 and protrusions 120 may be in any orientation with respect to each other. Examples of relevant factors include the shape, orientation, and/or configuration of the protrusions 21, 120, the shape, orientation, and/or configuration of the kit contents 200, and the materials used in at least one of the kit tray, kit retainer, and kit contents.

One advantage of the kit tray and retainer is that it may be used to accommodate, secure, and/or protect any combination of objects and/or kit contents. Thus, if the kit contents of a given kit, for example an enteral feeding kit, are changed, the same kit tray and kit retainer may be used to accommodate, secure, and/or protect the kit contents since the kit tray and kit retainer, and particular the kit retainer, will deform to accommodate the new contents. The same is true if the kit contents of a particular kit are rearranged within the kit tray.

The kit retainer or a portion thereof, for example the protrusions 120, may be injection molded out of polyethylene terephthalate-glycol-modified (PETG) (i.e., copolyester or polyester copolymer) or any other suitable material (or materials) and may be manufactured using any suitable method. Examples of suitable materials include acrylic, plastic, thermoplastic, rubber, metal, and/or glass. For example, at least a portion of the kit retainer may be made of a substantially rigid plastic such as 0.030 CL BAREX, or other materials that may be used as medical device packaging. Examples of suitable methods of manufacture include thermoforming, stamping, press-forming, injection molding, and/or machining. Various portions of the kit retainer may be made out of different materials (or mixtures of materials) and/or may be manufactured using different methods (e.g., the protrusions 120 may be made out of a thin, deformable material while other portions of the kit retainer 100 may be made out of a more rigid material). In another example, more than one method may be used to manufacture the kit retainer and/or a portion of the kit retainer.

Embodiments of the invention include a method of accommodating, securing, and protecting kit contents. The method may include providing one or more kit contents for a particular kit for use in a particular procedure, for example, medical kit contents for an enteral feeding kit for use in a enteral feeding procedure. The one or more kit contents may then be placed into a kit tray, for example, the kit content housing portion 20 of kit tray 1.

The kit contents may then be arranged in the kit tray 1, for example, by placing the kit contents so that they are separated or secured by one or more of the protrusions 21. Depending on the shape, orientation, and/or configuration of the protrusions 21 and/or kit contents, the kit contents may be placed with respect to the protrusions 21 in any desired manner. For example, some of the kit contents may be placed with respect to the protrusions 21 so that they form at least a loose snap-fit and/or press-fit with one or more of the protrusions. In another example, one or more of the protrusions 21 may be placed inside at least a portion of one or more of the kit contents. In a further example, one or more kit contents may be placed around one or more protrusions 21. In yet another example, one or more kit contents may be placed across one or more of the protrusions 21.

Once the kit contents are in the desired configuration in the kit tray 1, the kit retainer 100 may be placed in the kit tray 1. The interface portion 111 of the kit retainer 100 may be snap-fit, press-fit, and/or otherwise secured to the interface portion 22 of the kit tray 1 so that the kit retainer 100 and kit tray 1 stay together despite jostling during handling and/or transportation. During the process of securing the kit retainer 100 to the kit tray 1, the protrusions 120 (e.g., the bottoms 121 of the protrusions 120) on the kit retainer 100 may come into contact with the kit contents and begin to deform. As more pressure is applied to the kit retainer 100 so as to secure it to the kit tray 1, the protrusions 120 may continue to deform around the kit contents. Thus, when the kit retainer 100 and kit tray 1 are secured together and the pressure on the kit retainer 100 is released, the protrusions 120 may be deformed around portions of the kit contents so as to substantially restrict the movement of the kit contents, and thus the kit tray 1 and kit retainer is ready for handling and/or transportation.

When a user wishes to prepare the kit contents for use in a medical procedure, for example enteral feeding, the user may provide the kit containing the kit contents. The user may then remove the kit retainer 100 from the kit tray 1, for example, by causing the disengagement of the interface portion 111 from the interface portion 22. The interface portions 22, 111 may be disengaged from each other using any suitable method depending upon the configuration of the interface portions 22, 111. While the kit retainer 100 is being removed the kit tray 1, the protrusions 120 may begin to undeform if the protrusions 21, 120 are made out of a reversibly deformable material and substantially return to their predeformation shape. The protrusions 120, however, may not be made out of a reversibly deformable material.

Though the invention has been described in connection with a medical device kit, and particularly an enteral feeding kit, the invention is not so limited. The invention set forth herein may be used in conjunction with any other suitable medical or non-medical device, instrument, kit content, or procedure.

One of ordinary skill in the art will appreciate that other embodiments, in addition to embodiments set forth above, are apparent and are in keeping with the scope of the invention. For example, the kit tray 1 and/or kit retainer 100 may be comprised of one or more separate components. In another example, the dimensions, shapes, orientations, and/or configurations set forth herein for are exemplary only, and may be changed as desired and/or necessary (e.g., the protrusions 120 may be in the shape of a grid and/or have a substantially rectangular cross-section). In a further example, aspects of the embodiments may be combined and/or interchanged with other aspects of the embodiments (e.g., the protrusions 21 may be replaced with the protrusions 120 and vice versa). In yet another example, certain aspects of the embodiments may be removed (e.g., the kit tray 1 may not have protrusions 21). In a yet further example, aspects of the embodiments may be multiplied as desired (e.g., the kit tray 1 may have two working portions 10, one each on opposites sides of the housing portion 20).

Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. A packaging for a medical kit, comprising:
   a bottom configured to receive a plurality of medical products; and
   a top having at least one protrusion extending therefrom,
   wherein the bottom and the top are shaped so that the bottom receives the top with the at least one protrusion of the top extending towards the bottom,
   wherein the at least one protrusion is configured to deform about the plurality of medical products to restrict movement of the plurality of medical products,
   wherein the bottom includes at least one protrusion extending towards the top, the at least one protrusion of the bottom configured to loosely separate the plurality of medical products,
   wherein the bottom and the top are configured such that when the bottom receives the top, the at least one protrusion of the bottom is substantially transverse to the at least one protrusion of the top.

2. The packaging of claim 1, wherein the bottom is configured to loosely receive the plurality of medical products.

3. The packaging of claim 1, wherein the at least one protrusion of the top includes at least two protrusions having different shapes.

4. The packaging of claim 1, wherein the at least one protrusion of the bottom includes at least two protrusions having different shapes.

5. The packaging of claim 1, wherein the at least one protrusion of the top is comprised of PETG.

6. A packaging for a medical kit, comprising:
   a bottom configured to receive a plurality of medical products; and
   a top having at least one protrusion extending therefrom,
   wherein the bottom and the top are shaped so that the bottom receives the top with the at least one protrusion extending towards the bottom,
   wherein the at least one protrusion is configured to deform about the plurality of medical products to restrict movement of the plurality of medical products,
   wherein at least a portion of the top is configured to form a snap-fit with at least a portion of the bottom.

7. A packaging for a set of medical products, the packaging comprising:
   a housing portion configured to loosely receive the set of medical products; and
   a retaining portion configured to be secured to the housing portion with the set of medical products between the retaining portion and the housing portion;
   wherein the retaining portion has an initial configuration not corresponding to a configuration of the set of medical products, and wherein the initial configuration of the retaining portion is capable of changing as the retaining portion is secured to the housing portion to restrict movement of the set of medical products,
   wherein the retaining portion includes at least one protrusion configured to deform as the retaining portion is secured to the housing portion to restrict movement of the set of medical products,
   wherein the housing portion includes at least one protrusion configured to loosely receive the set of medical products, and
   wherein the housing portion and the retaining portion are configured such that when the housing portion receives the retaining portion, the at least one protrusion of the housing portion is substantially transverse to the at least one protrusion of the retaining portion.

8. The packaging of claim 7, wherein the initial configuration of the retaining portion is capable of changing as the retaining portion is secured to the housing portion to restrict movement of another set of medical products having a different configuration from the set of medical products.

9. The packaging of claim 7, wherein the at least one protrusion of the retaining portion includes at least two protrusions having different shapes.

10. The packaging of claim 7, wherein the at least one protrusion of the housing portion includes at least two protrusions having different shapes.

11. The packaging of claim 7, wherein the at least one protrusion of the retaining portion is comprised of PETG.

12. A packaging for a set of medical products, the packaging comprising:
   a housing portion configured to loosely receive the set of medical products; and
   a retaining portion configured to be secured to the housing portion with the set of medical products between the retaining portion and the housing portion;
   wherein the retaining portion has an initial configuration not corresponding to a configuration of the set of medical products, and wherein the initial configuration of the retaining portion is capable of changing as the retaining portion is secured to the housing portion to restrict movement of the set of medical products,
   wherein at least a portion of the housing portion is configured to form a snap-fit with at least a portion of the retaining portion.

13. A packaged medical kit, comprising:
   a plurality of medical products;
   a bottom containing the plurality of medical products; and
   a top received by the bottom and having at least one protrusion extending substantially toward the bottom, wherein the bottom is configured to loosely receive the plurality of medical products when the bottom has not received the top, wherein the at least one protrusion is deformed about the plurality of medical products to restrict movement of the plurality of medical products, wherein the bottom includes at least one protrusion extending towards the top, the at least one protrusion of the bottom configured to loosely separate the plurality of medical products when the bottom has not received the top, wherein the at least one protrusion of the bottom is transverse to the at least one protrusion of the top.

14. The packaged medical kit of claim 13, wherein the at least one protrusion of the top includes at least two protrusions having different shapes.

15. The packaged medical kit of claim 13, wherein the at least one protrusion of the bottom includes at least two protrusions having different shapes.

16. The packaged medical kit of claim 13, wherein the at least one protrusion of the top is comprised of PETG.

17. A packaged medical kit, comprising:
a plurality of medical products;
a bottom containing the plurality of medical products; and
a top received by the bottom and having at least one protrusion extending substantially toward the bottom,
wherein the bottom is configured to loosely receive the plurality of medical products when the bottom has not received the top,
wherein the at least one protrusion is deformed about the plurality of medical products to restrict movement of the plurality of medical products,
wherein at least a portion of the top is configured to form a snap-fit with at least a portion of the bottom.

18. A packaged medical kit, comprising:
a set of medical products;
a housing portion containing the set of medical products; and
a retaining portion secured to the housing portion with the set of medical products between the retaining portion and the housing portion;
wherein the retaining portion has an initial configuration not corresponding to a configuration of the set of medical products prior to the retaining portion being secured to the housing portion, and wherein the initial configuration of the retaining portion changes to correspond to the configuration of the set of medical products as the retaining portion is secured to the housing portion to restrict movement of the set of medical products,
wherein the retaining portion includes at least one protrusion that deforms as the retaining portion is secured to the housing portion to restrict movement of the set of medical products,
wherein the housing portion includes at least one protrusion that loosely receives the set of medical products prior to the retaining portion being secured to the housing portion,
wherein the housing portion and the retaining portion are configured such that when the housing portion receives the retaining portion, the at least one protrusion of the housing portion is substantially transverse to the at least one protrusion of the retaining portion.

19. The packaged medical kit of claim 18, wherein the at least one protrusion of the retaining portion includes at least two protrusions having different shapes.

20. The packaged medical kit of claim 18, wherein the at least one protrusion of the housing portion includes at least two protrusions having different shapes.

21. The packaged medical kit of claim 18, wherein the at least one protrusion of the retaining portion is comprised of PETG.

22. A packaged medical kit, comprising:
a set of medical products;
a housing portion containing the set of medical products; and
a retaining portion secured to the housing portion with the set of medical products between the retaining portion and the housing portion;
wherein the retaining portion has an initial configuration not corresponding to a configuration of the set of medical products prior to the retaining portion being secured to the housing portion, and wherein the initial configuration of the retaining portion changes to correspond to the configuration of the set of medical products as the retaining portion is secured to the housing portion to restrict movement of the set of medical products,
wherein at least a portion of the housing portion forms a snap-fit with at least a portion of the retaining portion.

23. A method of packaging a medical kit, comprising:
providing a packaging for a medical kit, comprising:
a bottom configured to receive a plurality of medical products; and
a top having at least one protrusion extending therefrom,
arranging the plurality of medical products in the bottom; and
securing the top to the bottom such that the at least one protrusion of the top extends toward the bottom and deforms about the plurality of medical products to restrict movement of the plurality of medical products,
wherein the bottom includes at least one protrusion extending towards the top, the at least one protrusion of the bottom configured to loosely separate the plurality of medical products,
wherein the bottom and the top are configured such that when the bottom receives the top, the at least one protrusion of the bottom is substantially transverse to the at least one protrusion of the top.

24. The method of claim 23, wherein securing the top to the bottom includes applying pressure to at least one of the top and the bottom.

25. A method of packaging a medical kit, comprising:
providing a packaging for a medical kit, comprising:
a bottom configured to receive a plurality of medical products; and
a top having at least one protrusion extending therefrom,
arranging the plurality of medical products in the bottom; and
securing the top to the bottom such that the at least one protrusion extends toward the bottom and deforms about the plurality of medical products to restrict movement of the plurality of medical products,
wherein securing the top to the bottom includes forming a snap-fit between the top and the bottom.

26. The method of claim 23, wherein arranging includes loosely arranging the plurality of medical products in the bottom.

27. A method of packaging a set of medical products, comprising:

providing a packaging for the set of medical products, the packaging comprising:
  a housing portion configured to loosely receive the set of medical products; and
  a retaining portion configured to be secured to the housing portion with the set of medical products between the retaining portion and the housing portion, the retaining portion having an initial configuration not corresponding to a configuration of the set of medical products;
providing the set of medical products;
arranging the set of medical products in the housing portion; and
securing the retaining portion to the housing portion such that the initial configuration of the retaining portion changes to correspond to the configuration of the set of medical products as the retaining portion is secured to the housing portion to restrict movement of the set of medical products,
wherein the housing portion includes at least one protrusion extending towards the top, the at least one protrusion of the housing portion configured to loosely separate the plurality of medical products,
wherein the housing portion and the retaining portion are configured such that when the housing portion receives the retaining portion, the at least one protrusion of the housing portion is substantially transverse to the at least one protrusion of the retaining portion.

28. The method of claim 27, wherein securing the retaining portion to the housing portion includes applying pressure to at least one of the retaining portion and the housing portion.

29. A method of packaging a set of medical products, comprising:
providing a packaging for the set of medical products, the packaging comprising:
  a housing portion configured to loosely receive the set of medical products; and
  a retaining portion configured to be secured to the housing portion with the set of medical Products between the retaining portion and the housing portion, the retaining portion having an initial configuration not corresponding to a configuration of the set of medical products;
providing the set of medical products;
arranging the set of medical products in the housing portion; and
securing the retaining portion to the housing portion such that the initial configuration of the retaining portion changes to correspond to the configuration of the set of medical products as the retaining portion is secured to the housing portion to restrict movement of the set of medical products,
wherein securing the retaining portion to th,e housing portion includes forming a snap-fit between the retaining portion and the housing portion.

30. The method of claim 27, wherein securing the retaining portion to the housing portion includes deforming at least one protrusion on the retaining portion around the set of medical products.

31. The method of claim 27, wherein arranging includes loosely arranging the plurality of medical products in the housing portion.

32. The packaging of claim 1, wherein at least a portion of the top is configured to form a snap-fit with at least a portion of the bottom.

33. The packaging of claim 7, wherein at least a portion of the housing portion is configured to form a snap-fit with at least a portion of the retaining portion.

34. The packaged medical kit of claim 13, wherein at least a portion of the top is configured to form a snap-fit with at least a portion of the bottom.

35. The packaged medical kit of claim 18, wherein at least a portion of the housing portion forms a snap-fit with at least a portion of the retaining portion.

36. The method of claim 23, wherein securing the top to the bottom includes forming a snap-fit between the top and the bottom.

37. The method of claim 27, wherein securing the retaining portion to the housing portion includes forming a snap-fit between the retaining portion and the housing portion.

* * * * *